(12) United States Patent
Crittenden (10) Patent No.: US 7,955,385 B2
(45) Date of Patent: Jun. 7, 2011

(54) DEVICE, SYSTEM, AND METHOD FOR AIDING VALVE ANNULOPLASTY (75) Inventor: James F Crittenden, Hollis, NH (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 463 days.

(21) Appl. No.: 11/069,335

(22) Filed: Feb. 28, 2005

(65) Prior Publication Data

US 2006/0195134 A1 Aug. 31, 2006

(51) Int. Cl.
*A61F 2/24* (2006.01)
(52) U.S. Cl. ........................... 623/2.36; 623/2.11
(58) Field of Classification Search .................. 606/108, 606/194; 623/2.11, 2.36–2.38
See application file for complete search history.

(56) References Cited

U.S. PATENT DOCUMENTS

| 6,029,671 | A | 2/2000 | Stevens et al. |
| 6,267,781 | B1 | 7/2001 | Tu |
| 6,361,759 | B1* | 3/2002 | Frayne et al. ............. 424/9.323 |
| 6,419,696 | B1* | 7/2002 | Ortiz et al. ................... 623/2.37 |
| 6,619,291 | B2 | 9/2003 | Hlavka et al. |
| 6,765,144 | B1 | 7/2004 | Wang et al. |
| 6,802,857 | B1 | 10/2004 | Walsh et al. |
| 2001/0034547 | A1* | 10/2001 | Hall et al. .................... 623/1.11 |
| 2002/0156526 | A1* | 10/2002 | Hlavka et al. ................ 623/2.11 |
| 2004/0243227 | A1 | 12/2004 | Starksen et al. |
| 2005/0149178 | A1 | 7/2005 | Spence |

FOREIGN PATENT DOCUMENTS

WO WO 01/47438 7/2001

* cited by examiner

*Primary Examiner* — Ryan J Severson (57) ABSTRACT

A device comprising a reference ring that may be temporarily disposed in abutment with the inferior perimeter surface of a heart valve to aid non-optical visualization of the valve annulus. The reference ring is elastically transformable between a straight delivery configuration and a generally circular or helical deployment configuration. The reference ring may include an inflatable portion that can be temporarily expanded on the inferior side of the valve annulus to deform the valve annulus into a temporary ledge or shelf for apposition with an annuloplasty ring. A system comprising a delivery catheter including a lumen with an exit port, the reference ring being slidably positionable within the lumen and being extendable from the exit port.

17 Claims, 8 Drawing Sheets

DEVICE, SYSTEM, AND METHOD FOR AIDING VALVE ANNULOPLASTY

TECHNICAL FIELD

This invention relates generally to medical devices and particularly to a device, system, and method for aiding implantation of a heart valve annuloplasty ring.

BACKGROUND OF THE INVENTION

Heart valves, such as the mitral and tricuspid valves, are sometimes damaged by diseases or by aging, which can cause problems with the proper function of the valve. The mitral and tricuspid valves consist of leaflets attached to a fibrous ring or annulus. In a healthy heart, the mitral valve leaflets overlap during contraction of the left ventricle, or systole, and prevent blood from flowing back into the left atrium. However, due to various cardiac diseases, the mitral valve annulus may become distended, causing the leaflets to remain partially open during ventricular contraction and thus allowing regurgitation of blood into the left atrium. This results in reduced ejection volume from the left ventricle, causing the left ventricle to compensate with a larger stroke volume. The increased workload eventually results in dilation and hypertrophy of the left ventricle, further enlarging and distorting the shape of the mitral valve. If left untreated, the condition may result in cardiac insufficiency, ventricular failure, and death.

A common repair procedure involves implanting an annuloplasty ring on the superior, or atrial, surface of the mitral valve annulus. The annuloplasty ring is aligned with the valve annulus and then fixedly attached to the valve annulus. The annuloplasty ring generally has a smaller diameter than the distended valve annulus, and when attached to the annulus, the annuloplasty ring draws the annulus into a smaller configuration, bringing the mitral valve leaflets closer together and providing improved valve closure during systole.

Catheter-based repair procedures for implanting an annuloplasty ring on the valve annulus require non-optical visualization of, at least, the heart valve and annuloplasty ring during placement of the ring at the valve annulus. As used herein, the phrase non-optical visualization refers to viewing an indirect image of body tissues and/or devices within a patient. Non-optical visualization of the valve annulus is challenging. Under fluoroscopy, the cardiac tissues do not appear, making it very difficult to accurately align the annuloplasty ring prior to its implantation. In many procedures, radiopaque contrast dye is used with x-ray imaging equipment to increase the visualization of the area of interest. However, when treating the mitral valve, repeated injections of contrast dye are not practical because of rapid wash-out in high-flow area being treated. Additionally, to make the high-volume contrast injections, the annuloplasty catheter system would require more lumens, larger lumens, or an additional catheter, none of which is desirable during catheterization procedures. Furthermore, multiple high-volume contrast injections are not desirable for the patient due to potential complications in the renal system, where the radiopaque contrast medium is filtered from the blood.

Other techniques for viewing images of cardiac structures include ultrasonography such as trans-thoracic echocardiography (TTE), trans-esophageal echocardiography (TEE), and cardiac magnetic resonance (CMR) including magnetic resonance imaging (MRI) or magnetic resonance angiography (MRA). However, none of the above techniques, used alone or in combination provides adequate visualization and guidance during catheter-based valve repair procedures.

Annuloplasty procedures are further challenged by the structure of the valve annulus. In particular, the mitral valve annulus lacks a definable shelf or ledge for conveniently locating an annuloplasty ring. The mitral valve leaflets are little more than flaps or appurtenances attached to the cardiac muscle tissue, creating a pseudo-annulus. During systole, the mitral valve is closed to form a relatively flat floor of the left atrium. However, during diastole, the mitral valve leaflets open towards the ventricular walls such that, in many cases, the valve annulus is not well defined. Since annuloplasty is performed on a beating heart, care must be taken during both systole and diastole when positioning an annuloplasty ring for fixation.

Without the direct optical visualization that is provided during surgery, it is difficult to position an annuloplasty ring in abutment with the superior surface of the valve annulus. With non-optical imaging techniques used during a catheter-based procedure, an annuloplasty ring may be inadvertently affixed in a misaligned position below, above or angled across the valve annulus. Affixing the annuloplasty ring in such a misaligned position could have negative consequences for the patient, such as increasing mitral regurgitation and/or triggering ectopic heart beats.

Therefore, it would be desirable to provide a device, system, and method for aiding implantation of an annuloplasty ring to overcome the aforementioned and other disadvantages.

SUMMARY OF THE INVENTION

One aspect of the present invention is a reference ring for aiding procedures such as catheter-based or other minimally invasive annuloplasty ring implantation. The reference ring may be temporarily disposed in abutment with the inferior perimeter surface, or compass of a cardiac valve and comprises imageable material to aid non-optical visualization of the valve annulus. The shape of the reference ring is pre-formed in the distal end of an elongate shaft and comprises a flexible jacket, a core positioned within the jacket and a marker disposed on at least one of the core and the jacket. The reference ring is elastically recoverable from a straight delivery configuration and a pre-formed, generally circular or helical deployment configuration.

The reference ring may include an inflatable portion that can be temporarily expanded on the inferior side of the valve annulus. The expanded portion of the reference ring deforms the valve annulus into a temporary ledge or shelf for improved apposition with an annuloplasty ring. Thus, the reference ring may provide a non-optical imaging aid for locating the valve annulus, and/or a physical aid for correctly positioning an annuloplasty ring with respect to the valve annulus.

Another aspect of the present invention is a system for aiding procedures such as catheter-based or other minimally invasive annuloplasty ring implantation. The system comprises a delivery catheter including a lumen with an exit port, and a reference ring having a straightened delivery configuration that is slidably positionable within the lumen. The reference ring is deployed through the exit port when the delivery catheter has been navigated to a target site. Upon exiting the catheter, the reference ring elastically coils into a pre-formed deployment configuration. The reference ring is pre-formed in the distal end of an elongate shaft. The proximal end of the shaft extends from the proximal end of the delivery catheter such that the clinician can manually translocate the reference ring between the straight delivery configuration and the pre-curved deployment configuration.

Yet another aspect of the present invention is a method of treating a cardiac valve. The method comprises delivering a reference ring in a straightened delivery configuration to an inferior ventricle position via a delivery catheter, extending the reference ring through an exit port of the delivery catheter, positioning a pre-curved portion of the reference ring in inferior abutment with an annulus of the heart valve and non-optically viewing at least a marked portion of the positioned reference ring.

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

BRIEF DESCRIPTION OF THE DRAWINGS

Similar reference numbers are used throughout the drawings to refer to similar parts.

DETAILED DESCRIPTION OF THE PRESENTLY PREFERRED EMBODIMENTS

One aspect of the present invention is a device having a non-optically visualizable reference ring for aiding in placement of an annuloplasty ring in abutment with a heart valve annulus. A visualization reference ring is designed to be temporarily positioned using intravascular catheterization techniques. Alternatively, surgical or minimally invasive, i.e. endoscopic techniques may be used to place the reference ring.

Figure 1:
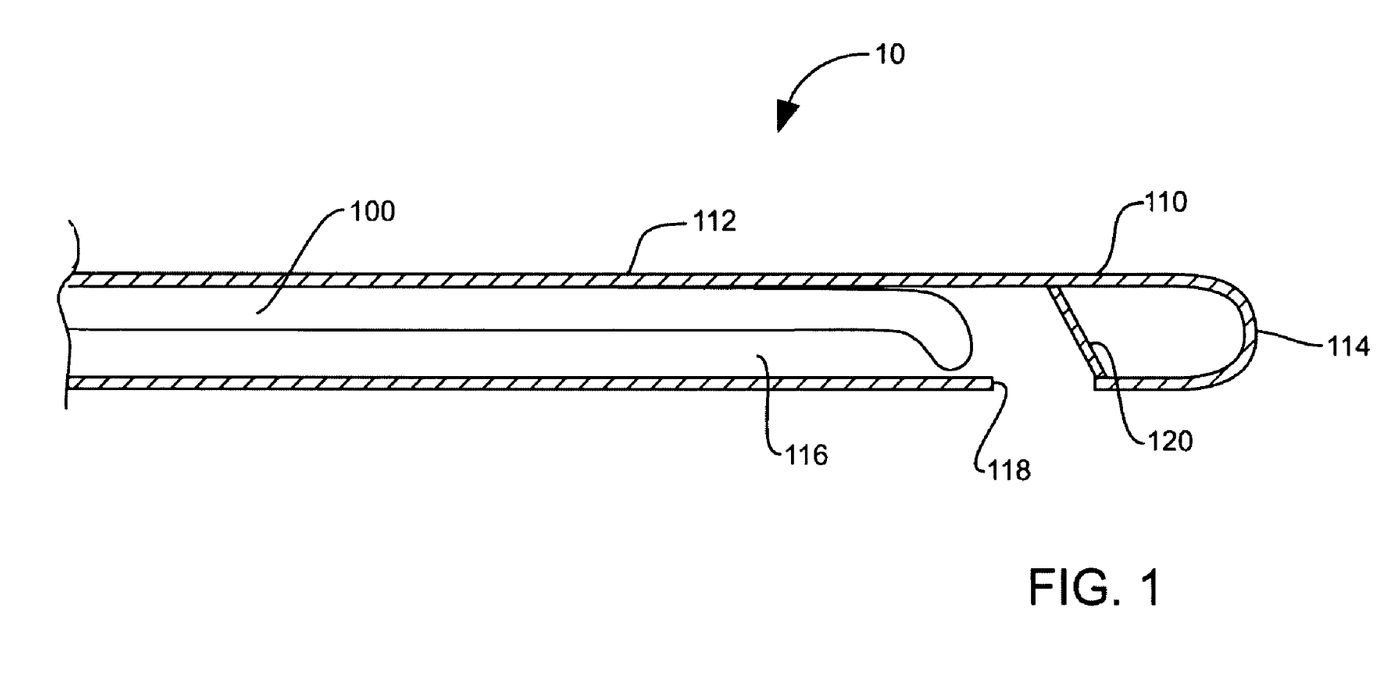
FIG. 1 is a longitudinal cross sectional illustration of a distal portion of a system for aiding valve annuloplasty, including a reference ring disposed within a delivery catheter, in accordance with the present invention.

FIG. 1 illustrates system 10 for aiding in non-optical visualization of a valve annulus during an annuloplasty procedure. System 10 includes delivery catheter 110 having lumen 116 for delivering non-optical visualization reference ring 100 there through. Reference ring 100 is pre-formed in a distal portion of an elongate shaft, the entire shaft being slidable within and optionally removable from lumen 116. Delivery catheter 110 includes catheter body 112 shown with rounded distal tip 114. Delivery catheter 110 may have a straight tip or a preformed or deflectable distal tip that is capable of assuming a desired bend with respect to the longitudinal axis of the catheter to aid in delivering reference ring 100. In one embodiment, distal tip 114 comprises a preset curve, e.g., a pigtail-shaped tip as such curves are known in the catheter art (see FIG. 8). Pigtail-shaped catheter tips are known to facilitate crossing an aortic valve and to minimize ectopic heartbeats when located within the left ventricle.

Catheter body 112 comprises one or more flexible, biocompatible polymeric materials such as polyurethane, polyethylene, polyamide, fluoropolymers such as fluorinated ethylene propylene (FEP) or polytetrafluoroethylene (PTFE), or polyether-block amide (PEBA) co-polymer. Catheter body 112 is sufficiently flexible to navigate the vasculature from an entry site to a location within the heart, while having sufficient stiffness to constrain the pre-formed curvature of reference ring 100 in the relatively straight delivery configuration. Delivery catheter 110 further comprises exit port 118. In one embodiment, exit port 118 comprises a side port. Alternatively, exit port 118 may be an axially aligned end port (not shown) disposed at distal tip 114. Reference ring 100 exits delivery catheter 110 via port 118. As shown in FIG. 1, wherein exit port 118 comprises a side port, ramp 120 is provided within lumen 116 and is positioned distal to and adjacent port 118 to deflect reference ring 100 towards and through exit port 118, and out of delivery catheter 110. Ramp 120 is not required in the embodiment wherein exit port 118 is an axially aligned end port.

The terms "distal" and "proximal" are used herein with reference to the treating clinician during deployment of the device; "Distal" indicates an apparatus portion distant from, or a direction away from the clinician and "proximal" indicates an apparatus portion near to, or a direction towards the clinician. The discussion below relates to placement of visualization reference ring 100 in inferior abutment with a mitral valve annulus. However, those with skill in the art will recognize that visualization reference rings of the invention may also be deployed at other cardiac valves or other locations in the body and may be used to visualize other openings or other structures within the body.

Visualization reference ring 100 comprises one or more materials that are viewable by radiography, ultrasound, or magnetic resonance imaging visualization techniques. In some embodiments, reference ring 100 comprises a combination of materials that allows for viewing an image of the device using two or more of the above-mentioned techniques. Specific embodiments of reference ring 100 are discussed below in relation to FIGS. 2 to 7.

Figure 2:
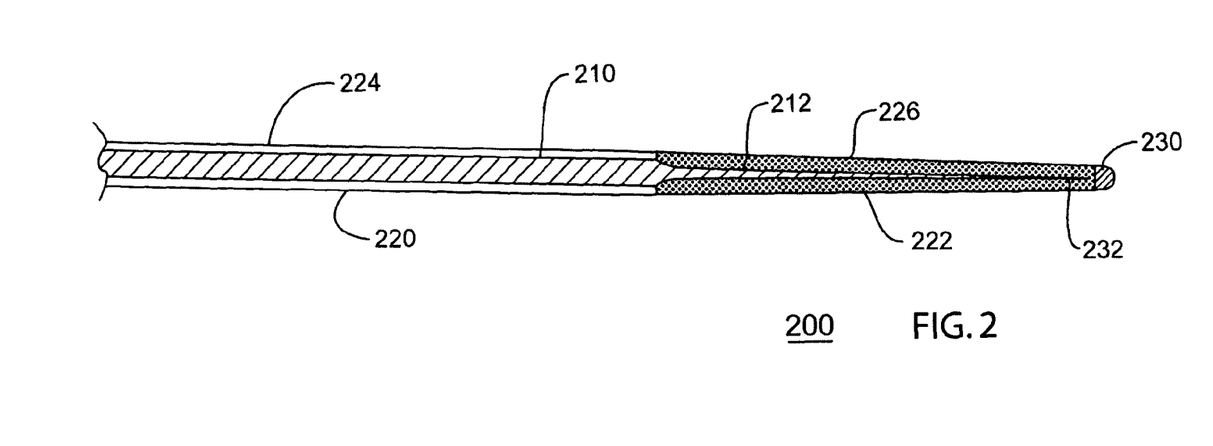
FIGS. 2-7 are longitudinal cross sectional illustrations of different embodiments of the reference ring of FIG. 1, shown in a straight delivery configuration.

FIG. 2 illustrates one embodiment of visualization reference ring 200, in accordance with the invention. Reference ring 200 is illustrated in its straightened delivery configuration, as it would appear when constrained within delivery catheter 110. Reference ring 200 is formed in a distal portion of an elongate shaft that extends through lumen 116 of delivery catheter 110. A proximal end of the elongate shaft extends proximally out of delivery catheter 110, where the shaft can be manipulated by the practitioner. As it is deployed from a delivery catheter, reference ring 200 returns to a pre-formed, generally circular or helical deployment configuration (see FIGS. 8-11). During the annuloplasty procedure, reference ring 200 is placed in an inferior position adjacent the mitral valve annulus to aid in non-optical visualization of the annulus during placement of an annuloplasty ring on the superior side of the mitral valve. The methods of deployment of the reference ring of the invention are discussed in more detail below with reference to FIGS. 8-11.

Reference ring 200 comprises core 210 and jacket 220 positioned about a portion of core 210. Core 210 includes distal end portion 212, which may be tapered or otherwise reduced in diameter to provide a more flexible portion that facilitates atraumatic formation of the curved deployment configuration in a patient's ventricle. Tip 230 is secured to distal end portion 212, either directly or by an attached core extension such as tether 232. In this example as illustrated, the tip 230 is a blunt and rounded tip. Core 210 comprises a material that may elastically transition from the relatively straight delivery configuration to the pre-formed deployment configuration. The material of core 210 may be a thermal shape memory material that attempts to assume the deployment configuration upon exposure to a patient's body temperature or with application of heat from other sources such as a warm flushing solution or a built-in heating element (not shown). The material of core 210 also may have sufficient elasticity be bent from the pre-formed deployment configuration to the straight delivery configuration without plastic deformation. Core 210 may be composed of a biocompatible metal such as nitinol, stainless steel, or age-hardenable nickel-cobalt-chromium-molybdenum alloy. Core 210 may also comprise biocompatible engineering plastics, such as amides, polyimides, polyolefins, polyesters, urethanes, thermoplastics, thermoset plastics, and blends, laminates or copolymers thereof. Core 210 may comprise a radiopaque material or may include radiopaque markers (see FIG. 4) disposed along its length.

Jacket 220 is disposed around core 210 and may comprise material that is viewable via radiography, i.e. material that is radiopaque under fluoroscopic or radiographic imaging. FIG. 2 illustrates jacket 220 having distal portion 222 and optional proximal portion 224. Jacket 220 may have a constant diameter along its length or it may taper towards tip 230 along distal portion 222. In the embodiment illustrated, distal portion 222 comprises coil 226 disposed about core 210. A distal end of coil 226 is fixedly attached to tip 230. A proximal end of coil 226 is fixedly attached to core 210 and/or to optional proximal portion 224 of jacket 220 by welding, adhesive or any other method known to those with skill in the art. Coil 226 may comprise material similar to those materials well known in the art for medical guide wires, especially small diameter guide wires. Coil 226 may be entirely radiopaque or may include spaced-apart radiopaque markers. The entire coil or the markers may be composed of radiopaque materials such as platinum, platinum alloys, gold or combinations thereof. Coil 226 may have an outer diameter that remains constant or tapers towards tip 230. Coil 226 may be disposed around distal portion 222 in a single layer or may comprise multiple layers. Optional proximal portion 224 of jacket 220 may comprise a continuation of distal portion 222, or jacket portion 224 may be an outer sleeve comprising materials similar to those described above regarding core 210. As a non-limiting example, proximal portion 224 may comprise a low-friction polymer jacket that surrounds core 210 comprising metal.

Figure 3:
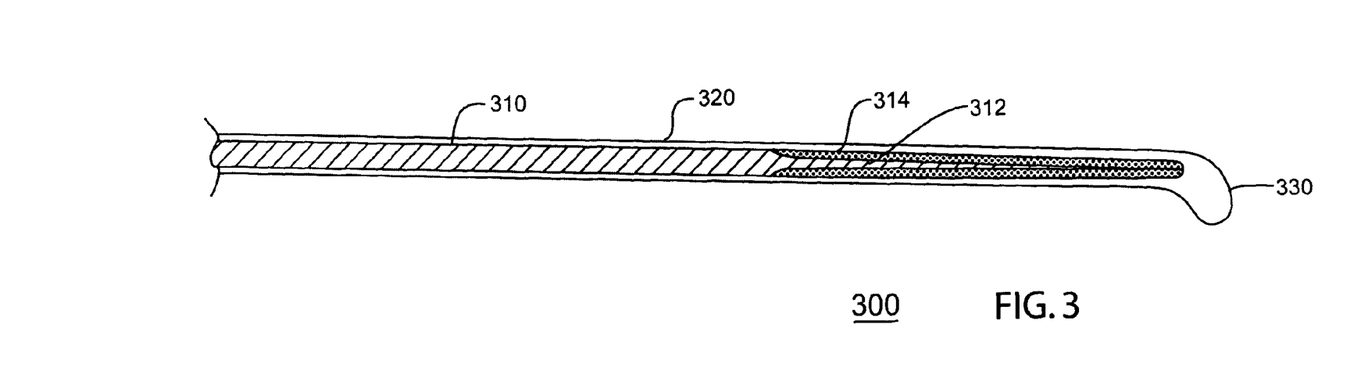

FIG. 3 illustrates another embodiment of a non-optical visualization reference ring 300, in accordance with the invention. To aid in positioning reference ring 300, it may be desirable to have reference ring 300 be visible using one or more imaging means including, but not limited to, radiography, fluoroscopy, echocardiography, or magnetic resonance imaging (MRI). FIG. 3 illustrates reference ring 300 including a radiopaque component and at least a second component comprising either an echogenic material or a material that is visible under MRI such that reference ring 300 can be visualized using various techniques, either alternatively or simultaneously.

Visualization reference ring 300 comprises core 310, jacket 320 positioned about core 310, and tip 330. Core 310 comprises a core wire having a tapered distal end portion 312. Core 310 is composed of a material such as those materials discussed above regarding core 210. In this embodiment, coiled spring 314 is wrapped about tapered distal end portion 312. Core 310 and/or coiled spring 314 may be entirely or partially composed of radiopaque material.

Jacket 320 encases core 310 and coil spring 314. Jacket 320 may be formed around core 310 in any manner that is well known in the art. In one embodiment, jacket 310 is formed around core 310 by placing core 310 within a mold cavity and injection molding or casting material about core 310 to produce the final structure of reference ring 300. Alternative methods of forming jacket 320 include applying a solvent-based slurry to core 310 using either spraying or dipping techniques. Another method of forming jacket 320 includes shrink fitting a thermoplastic sleeve about core 310, using either a permanent shrink tube to form the sleeve, or using shrink tubing as a removable tool surrounding a sleeve formed of another thermoplastic material. Combinations of the above methods are also useful, such as applying a coating of non-optical visualizing material about core 310 and spring 314, then providing a non-filled polymer cover to seal the coating.

In one embodiment of reference ring 300, jacket 320 may comprise an echogenic material, such as closed cell foam, microporous, mezoporous or other porous material deposited around core 310 and coiled spring 314. In another embodiment, jacket 320 may be a polymer jacket composed of a biocompatible polymer, such as, for example, polyurethane, polyethylene, polyamide, PEBA co-polymer, or fluoropolymers such as FEP or PTFE as are described above for possible use in catheter body 112. In one embodiment, jacket 320 comprises a polymer having a plurality of embedded micro bubbles or a microporous surface structure, such as ECHO-COAT® medical imaging coating by Angiotech BioCoatings, Inc. of Henrietta, N.Y., U.S.A. The micro pores of such materials are readily visualized using ultrasonographic techniques.

In another embodiment, jacket 320 may contain one or more MRI-visible components such as ferromagnetic, paramagnetic or diamagnetic particles, or compounds found in liquid MRI contrast agents. These injectable or orally administered agents include, but are not limited to, ultrasmall superparamagnetic iron oxide (USPIO), e.g. Combidex® positive contrast agent by Advanced Magnetics, Inc. of Cambridge, Mass. U.S.A., or negative contrast agents such as low-molecular-weight gadolinium chelate, gadolinium tetraazacyclododecanetetraacetic acid (Gd-DOTA) or perfluoroctylbromide (PFOB). Alternatively, jacket 320 may encompass helical and ring structures (not shown) arranged such that an applied electromagnetic field will induce radiation of an electromagnetic field that improves visualization of a medical device under MRI, as taught in U.S. Pat. No. 6,802,857 entitled MRI Stent.

Jacket 320 ends at distal tip 330. Distal tip 330 may be integral with jacket 320 and composed of the same material. Tip 330 may be radially curved or olive-shaped (not shown) to aid in navigating visualization reference ring 300 between the inside surface of the ventricle and the chordae tendinae or valve leaflets as the device is positioned beneath the cardiac valve. In another embodiment, tip 330 may form a J-shaped bend toward the center of the helix or ring upon deployment from the delivery catheter.

Figure 4:
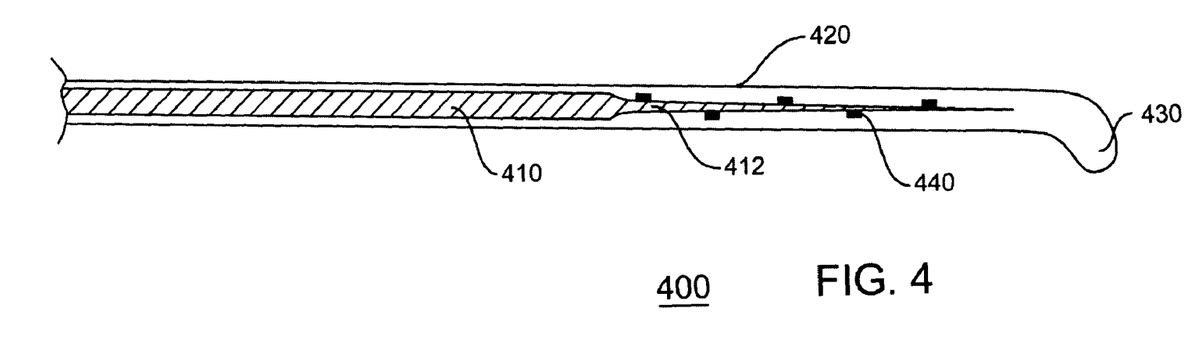

FIG. 4 illustrates another embodiment of a non-optical visualization reference ring 400, in accordance with the invention. Visualization reference ring 400 comprises core 410, jacket 420 positioned about core 410, and tip 430. Similar to the embodiments described above, core 410 includes a tapered distal end 412. Core 410 may be composed of a radiopaque material as described above or may be composed of another material that is not radiopaque. Tapered distal end 412 includes a plurality of spaced apart radiopaque markers 440 disposed along the tapered end. Markers 440 may be small elements that do not extend around core 410, or they may be rings (not shown) that encircle core 410. Markers 440 may be placed at specific intervals or may be irregularly spaced along core 410. In one embodiment, each marker 440 is placed a specified distance from the next marker to provide an in-vivo scale for use in estimating the size of the annulus once the visualization reference ring 400 is in place abutting the cardiac valve. Jacket 420 is composed of an echogenic or MRI visible material similar to those described above for jacket 320.

Figure 5:
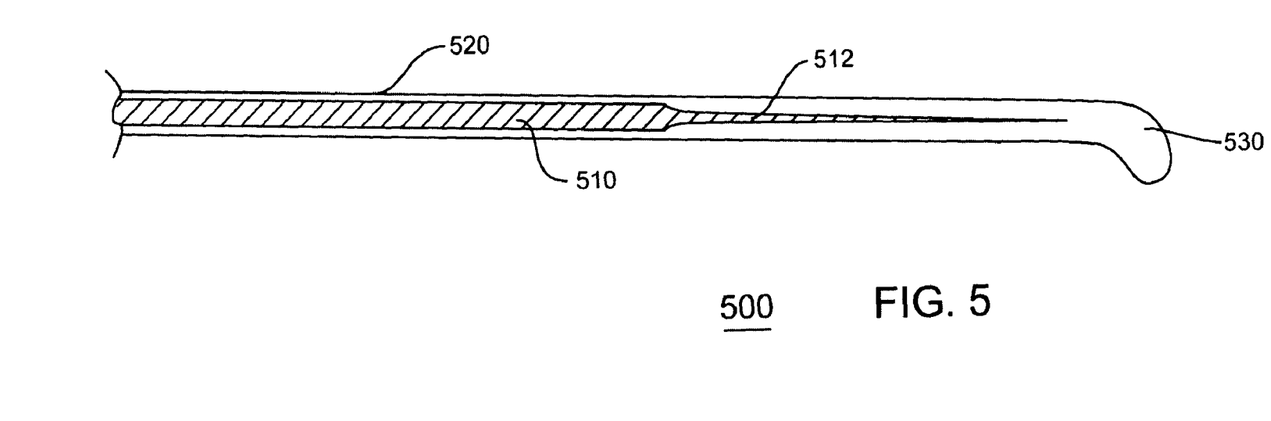

Non-optical visualization reference ring 500, illustrated in FIG. 5, does not include markers, but is otherwise similar to visualization reference ring 400, including jacket 520 positioned about core 510, tapered distal end 512, and tip 530. In one embodiment, core 510 may be composed of radiopaque material. In another embodiment, core 510 may be composed of a non-radiopaque material.

Figure 6:
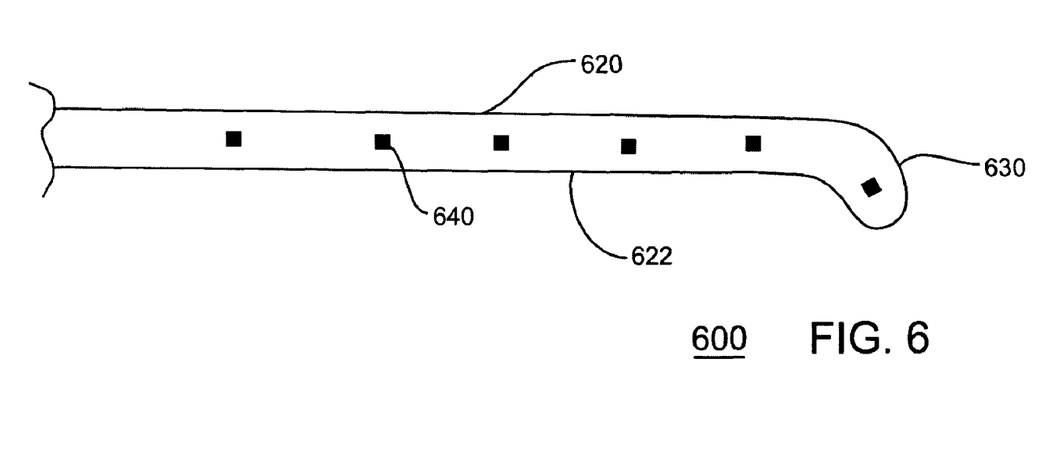

FIG. 6 illustrates non-optical visualization reference ring 600. Visualization reference ring 600 comprises jacket 620, curved tip 630, and a plurality of markers 640. Jacket 620 comprises a biocompatible polymeric material that is suitable for visualization using ultrasonographic or MRI techniques. In one embodiment, reference ring 600 comprises an echogenic, porous material and/or an MRI visible material 622. Reference ring 600 further includes a core composed of a plurality of radiopaque markers embedded in jacket 620. In the embodiment shown, markers 640 are arranged in a uniformly spaced linear pattern within reference ring 600. Reference ring 600 may be molded by any manner that is known to those with skill in the art.

Figure 7:
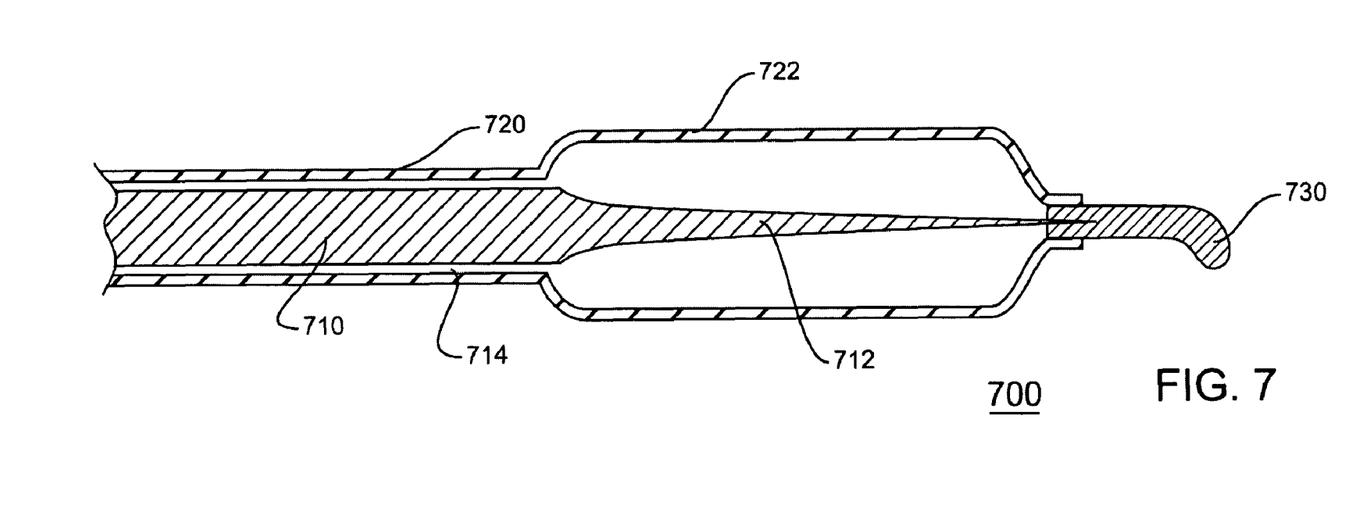

FIG. 7 illustrates another embodiment of a non-optical visualization reference ring 700 in accordance with the invention. Reference ring 700 is visible using fluoroscopy, echocardiography, MRI or another means of visualization to aid in positioning. Additionally, visualization reference ring 700 is expandable on the inferior side of the cardiac valve annulus to deform the valve leaflets during diastole, thus providing a better-defined valve annulus, which acts as a structural shelf to aid in positioning the annuloplasty device on the superior side of the valve. Visualization reference ring 700 comprises core 710 and jacket 720. Core 710 includes a tapered distal portion 712 that terminates within soft distal tip 730. Core 710 comprises a material, as described in the above embodiments, suitable for elastically re-shaping into the deployment configuration upon exiting the delivery catheter.

Elongate balloon 722 is disposed around a distal portion of core 710 and may be formed as an enlarged distal portion of jacket 720. As shown in FIG. 7, the distal end of balloon 722 is sealingly fixed to distal tip 730. Balloon 722 may have a length longer than, shorter than, or matching the compass of a cardiac valve. The elongate annular space between core 710 and jacket 720 defines inflation lumen 714, which fluidly communicates the interior of balloon 722 to a connector fitting (not shown) at the proximal ends of core 710 and jacket 720. Alternatively, all or part of inflation lumen 714 may be formed alongside core 710 or in any other practical arrangement known to those of skill in the balloon catheter art. Balloon 722 may be inflated with any suitable fluid, such as sterile saline, radiopaque contrast medium or liquid MRI imaging agents as described above. Balloon 722 may also be inflated with gas such as carbon dioxide, which is advantageously rapidly miscible in blood in the event of leakage.

Balloon 722 may be manufactured from inelastic polymers such as polyurethane, polyethylene, polyethylene terephthalate (PET), polyamide, PEBA co-polymer, and blends or laminates thereof. Alternatively, balloon 722 may be made from an elastic material such as latex, or silicone or other synthetic rubbers. With balloon 722 deflated, reference ring 700 fits slidably within lumen 116 of delivery catheter 110 and may be passed in and out of catheter 110 through exit port 118. Once visualization reference ring 700 has been placed in inferior abutment to the cardiac valve annulus, then balloon 722 is inflated. The inflated balloon alters the shape of the valve leaflets during diastole to provide a temporary structural shelf that will aid the clinician in properly placing an annuloplasty device, as will be discussed in more detail below.

Figure 8:
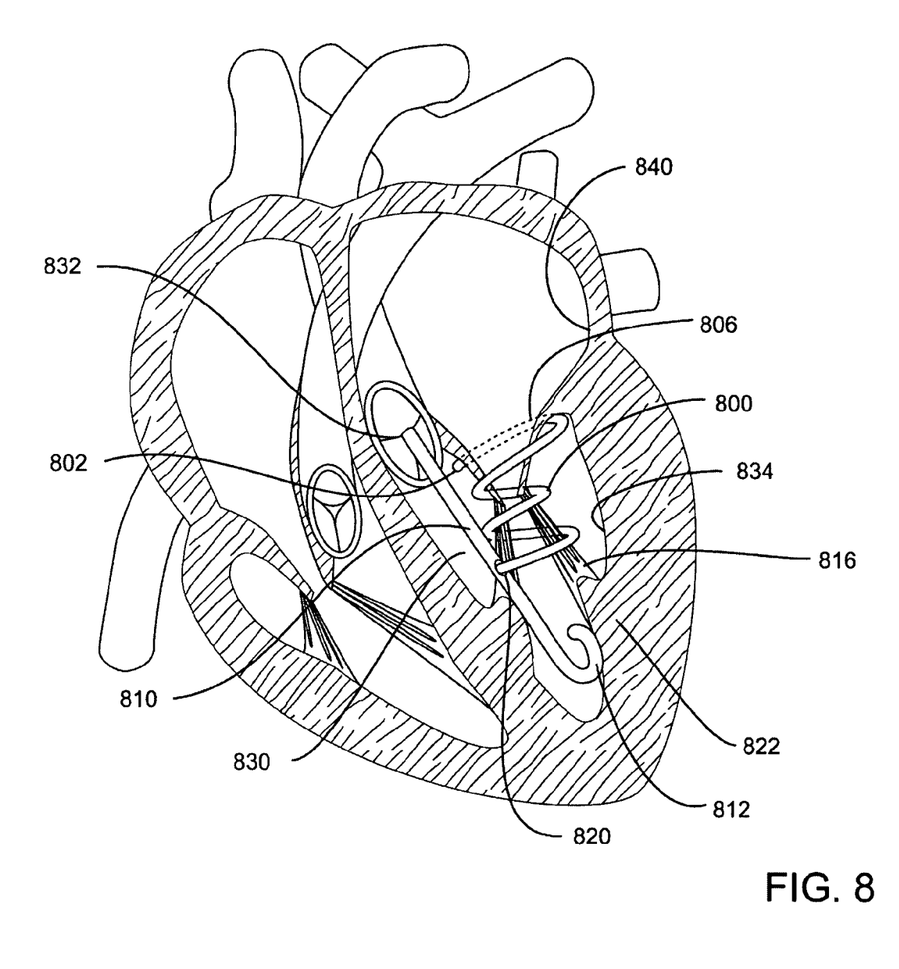
FIGS. 8 and 9 are transverse cross sectional illustrations of a heart, showing the deployment of different embodiments of the reference ring of FIG. 1 into inferior abutment with a mitral valve annulus.
Figure 9:
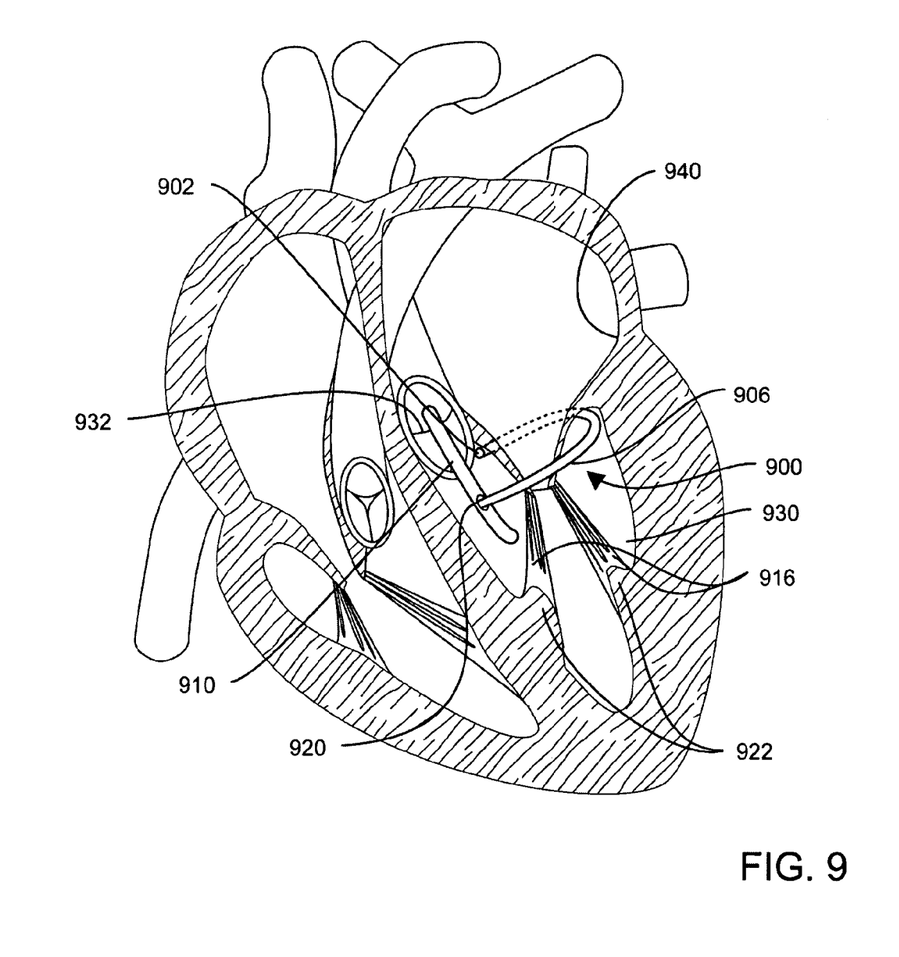

FIGS. 8 and 9 illustrate that non-optical visualization reference rings of the present invention may form a generally helical or circular shape upon deployment from the delivery catheter. FIG. 8 illustrates an embodiment of visualization reference ring 800 that forms a helix upon deployment from the delivery catheter. Reference ring 800 may be any one of the embodiments described above and shown in FIGS. 1 to 7, wherein the reference rings are illustrated in their straightened delivery configurations. Reference ring 800 includes a core/jacket portion of sufficient length to form a helical reference ring having at least two turns, the most distal turn being placeable in an abutment position inferior to a mitral valve annulus where the valve leaflets are attached to the surrounding cardiac tissue.

In this embodiment, reference ring 800 is delivered to the left ventricle disposed within delivery catheter 810. Delivery catheter 810 is advanced through aortic valve 832 into left ventricle 830. Delivery catheter 810 includes a pig-tail distal end 812, as is commonly found on ventriculography catheters. Pig-tail distal end 812 may be advanced to an apical position within the left ventricle near, or in contact with papillary muscle 822. Apical positioning of pig-tail distal end 812 helps to stabilize delivery catheter 810 within the beating heart.

Once delivery catheter 810 is stably positioned, reference ring 800 is advanced distally within catheter 810 to pass through exit port 820 and into left ventricle 830. Upon exiting port 820, reference ring 800 elastically recovers its preformed, helical deployment configuration. Continued advancement of visualization reference ring 800 from delivery catheter 810 causes distal end 802 to travel a generally circular route around left ventricle 830, passing through the annular space formed between left ventricular wall 834 on the outside and the mitral valve leaflets or chordae tendinae 816 on the inside. Visualization reference ring 800 is advanced until most distal turn 806 of the helix is located in inferior apposition to mitral valve annulus 840. The helical shape of reference ring 800 allows it to expand and contract like a coil spring to accommodate ventricular contractions while maintaining the desired apposition of most distal turn 806 beneath mitral valve annulus 840.

FIG. 9 illustrates visualization reference ring 900 that forms an open circle at a position inferior to the mitral valve annulus upon deployment from the delivery catheter. In this embodiment, delivery catheter 910 is advanced through aortic valve 932 until exit port 920 is positioned within left ventricle 930. Exit port 920 may be located superiorly of papillary muscles 922. Once delivery catheter 910 is positioned correctly, visualization reference ring 900 is advanced distally through delivery catheter 910 to extend through exit port 920 and into left ventricle 930. Upon exiting from port 920, visualization reference ring 900 resumes its pre-formed, circular deployment configuration. Continued advancement of visualization reference ring 900 from delivery catheter 910 causes distal end 902 to travel a generally circular route around left ventricle 930, passing through the annular space formed between left ventricular wall 934 on the outside and the mitral valve leaflets or chordae tendinae 916 on the inside. Visualization reference ring 900 is advanced until reference ring portion 906 is located in inferior apposition to mitral valve annulus 940.

Figure 10:
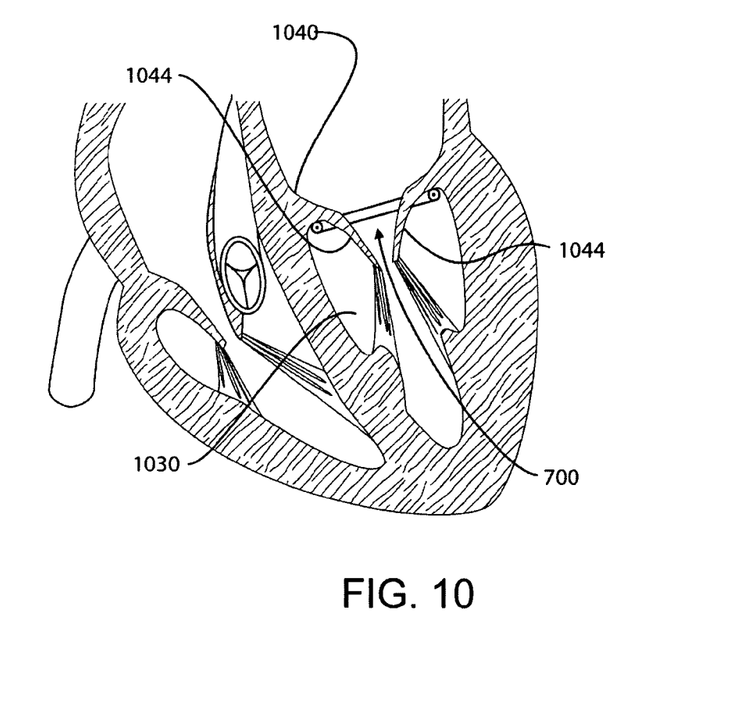
FIG. 10 is a transverse cross sectional illustrations of a heart illustrating the reference ring of FIG. 7 located in inferior abutment with a mitral valve annulus.
Figure 11:
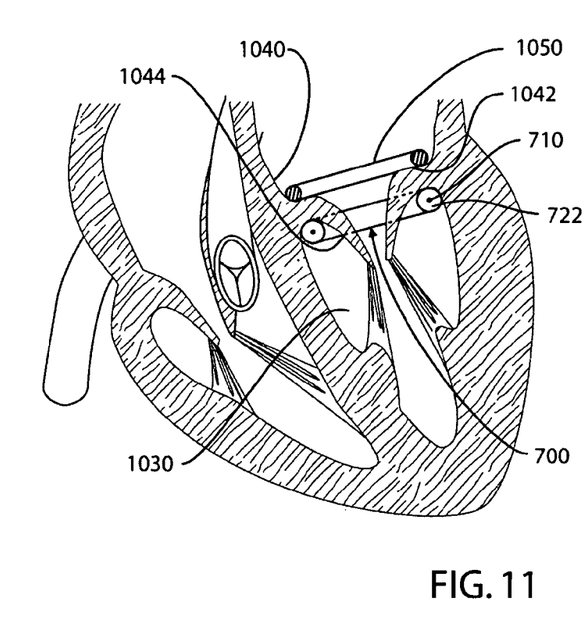
FIG. 11 is a transverse cross sectional illustrations of a heart illustrating the reference ring of FIG. 7 and an associated annuloplasty ring within the respective heart chambers.

FIGS. 10 and 11 illustrate the placement of visualization reference ring 700 in the heart. For clarity, FIGS. 10 and 11 illustrate only the most distal portion or turn of visualization reference ring 700. Reference ring 700 may be delivered to left ventricle 1030 in a manner similar to that illustrated in FIGS. 8 or 9. As described above, reference ring 700 includes elongate balloon 722 disposed about core wire 710. Balloon 722 may be inflated once reference ring 700 is placed at an inferior position abutting mitral valve annulus 1040. Inflation of balloon 722 forces valve leaflets 1044 to wrap around reference ring 700, thus expanding or extending valve annulus 1040 in a radially inward direction. Shelf-like protrusion 1042 thus created temporarily provides an enlarged target and structural support for placement of annuloplasty ring 1050 during an annuloplasty procedure. In practice, the clinician rests annuloplasty ring 1050 on shelf-like protrusion 1042 while annuloplasty ring 1050 is being secured in place. Once annuloplasty ring 1050 has been secured to the cardiac tissues adjacent valve annulus 1040, balloon 722 is deflated and visualization reference ring 700 is retracted back into the delivery catheter (not shown).

Figure 12:
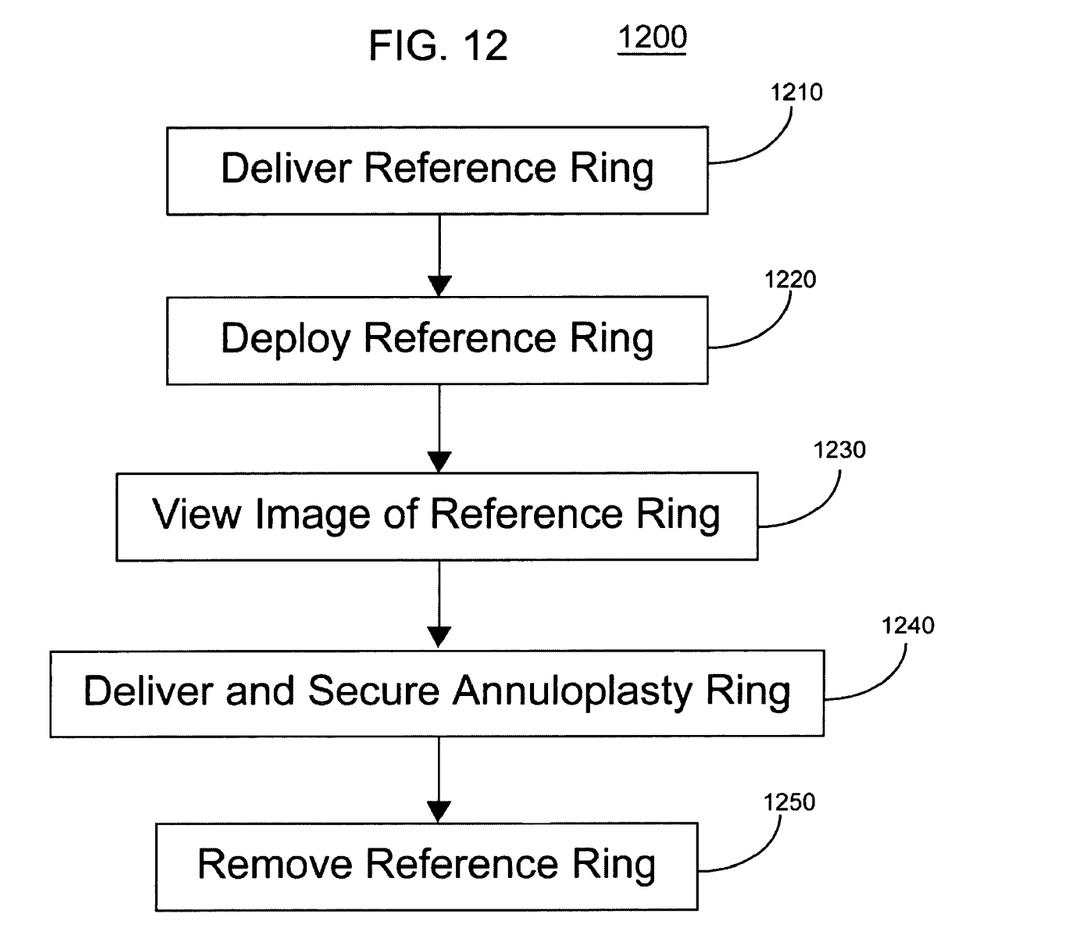
FIG. 12 is a flow diagram of one method of using a reference ring, in accordance with the present invention.

Another aspect of the present invention is a method of aiding annuloplasty ring implantation. FIG. 12 shows a flow diagram of one embodiment of method 1200 in accordance with the present invention. A reference ring is delivered in a lumen of a delivery catheter proximate a valve annulus (Block 1210). In the present embodiment, the reference ring and delivery catheter are those comprising system 10, as described above.

For delivery, system 10 is in the configuration shown in FIG. 1, with non-optical visualization reference ring 100 being slidably received within delivery catheter 110. Delivery catheter 110, carrying reference ring 100, is navigated through a patient's circulatory system and catheter distal tip 114 is passed into the left ventricle. This may be accomplished by inserting delivery catheter 120 into and through the femoral artery into the aorta, through the aortic valve and into the left ventricle. Other paths are available, as are known to those with skill in the art. For minimally invasive techniques or surgical approaches with an open chest, the delivery catheter may be replaced by an elongate element such as an endoscope, trocar or cannula, which may be inserted directly into the ascending aorta. The elongate element can then follow the same path as the catheter-based procedure to reach the left ventricle.

Visualization reference ring 100 is then deployed (Block 1220) by advancing reference ring 100 within the delivery catheter, through exit port 118, and into the left ventricle, as is seen in FIGS. 8 and 9. The distal tip of reference ring 100 is advanced until the most distal portion of reference ring 100 is placed in inferior abutment to the mitral valve annulus, as is seen in FIGS. 8 and 9. In another embodiment of a method of the present invention, a balloon portion of the visualization reference ring is inflated to produce a shelf-like protrusion at the valve annulus, as shown in FIGS. 10 and 11.

The deployment and placement of reference ring 100 at the target site inferiorly apposed to the mitral valve annulus is viewed by non-optical methods known to those with skill in the art (Block 1230). The image of reference ring 100 may be viewed using fluoroscopy, ultrasonography such as trans-thoracic echocardiography (TTE), trans-esophageal echocardiography (TEE), and cardiac magnetic resonance (CMR) including magnetic resonance imaging (MRI) or magnetic resonance angiography (MRA), or another means of visualization to aid in positioning.

Next, an annuloplasty ring is secured to the valve annulus (Block 1240). Once the visualization reference ring is properly positioned, an annuloplasty device, such as, for example, an annuloplasty ring known in the art, is advanced to the cardiac valve annulus, positioned in parallel alignment with the reference ring, and secured in position by any method known to those with skill in the art. The annuloplasty ring may comprise materials that are viewable under the same imaging techniques that can be used to visualize the reference ring. Thus, under one or more selected non-optical visualization techniques, the clinician can simultaneously view both the annuloplasty ring and the reference ring to aid in manipulating the annuloplasty ring into close parallel alignment with the reference ring before implanting the annuloplasty ring. When properly aligned, the annuloplasty ring and reference ring will be separated by only the thickness of the valve leaflets comprising the pseudo-annulus of the mitral valve. To attain close parallel alignment with each other, the reference ring can be pre-formed in the size and shape of the annuloplasty ring. Thus, distal helical turn 806 and reference ring portion 906 may be slightly non-circular to mimic the approximate D-shape of the mitral valve and an annuloplasty ring sized to fit the valve.

Visualization reference ring 100 is removed following implantation of the annuloplasty ring (Block 1250). Reference ring 100 is withdrawn into the delivery catheter before both components of the system are removed from the patient. In another embodiment of a method utilizing visualization reference ring 700 illustrated in FIG. 7, balloon 722 is deflated prior to retracting reference ring 700.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A device for aiding implantation of a heart valve annuloplasty ring, the device comprising an elongate flexible shaft having a reference ring defined along a distal portion thereof, the reference ring being elastically deformable from a pre-formed deployment configuration to a straight delivery configuration, the deployment configuration having at least one coil approximating a size and shape of the annuloplasty ring, the elongate flexible shaft having a proximal end sized to extend proximally out of a delivery catheter, wherein the at least one coil of the distal portion of the reference ring comprises a permanent jacket affixed to and permanently encasing a core, the reference ring having a blunt and rounded distal tip, and wherein the reference ring is configured to retract into a delivery catheter after implantation of the annuloplasty ring.

2. The device of claim 1 wherein the reference ring comprises a material viewable by at least one imaging technique selected from a group consisting of radiography, fluoroscopy, ultrasonography, trans-thoracic echocardiography (TTE), trans-esophageal echocardiography (TEE), cardiac magnetic resonance (CMR), magnetic resonance imaging (MRI) and magnetic resonance angiography (MRA).

3. The device of claim 1 wherein the reference ring includes at least one marker.

4. The device of claim 1 wherein the deployment configuration comprises a helix.

5. The device of claim 1 wherein the core has a tapered distal end.

6. The device of claim 1 wherein the core comprises a biocompatible material chosen from a group consisting of nitinol, stainless steel, age-hardenable nickel-cobalt-chromium-molybdenum alloy, engineering plastic, amides, polyimides, polyolefins, polyesters, urethanes, thermoplastics, thermoset plastics, and blends, laminates or copolymers thereof and combinations thereof.

7. The device of claim 1 wherein the jacket comprises a porous material viewable under ultrasonography.

8. The device of claim 1 wherein the jacket comprises a material chosen from a group consisting of ferromagnetic, paramagnetic and diamagnetic particles, and ultrasmall super-paramagnetic iron oxide (USPIO), low-molecular-weight gadolinium chelate, gadolinium tetraazacyclododecanetetraacetic acid (Gd-DOTA) and perfluor-octylbromide (PFOB).

9. The device of claim 1 wherein the jacket comprises a balloon and the flexible shaft has an inflation lumen fluidly communicating an interior of the balloon to a fitting located at a proximal end of the device.

10. The device of claim 1 wherein the blunt and rounded distal tip is a soft tip.

11. A system for aiding implantation of a heart valve annuloplasty ring, the system comprising:
   an elongate delivery catheter having proximal and distal ends, an exit port adjacent the catheter distal end and a lumen extending from the exit port to the proximal end; and
   the elongate shaft of claim 1 being slidably disposed within the catheter lumen, the reference ring being extendable through the catheter exit port and having the straight delivery configuration constrainable by the delivery catheter, the elongate shaft having a proximal end extending proximally out of the elongate delivery catheter, wherein the reference ring is configured to retract into a delivery catheter after implantation of the annuloplasty ring.

12. The system of claim 11 wherein the exit port is a side port.

13. The system of claim 12 wherein the catheter includes a ramp disposed in the lumen, the ramp being positioned and angled to align the reference ring with the exit port.

14. The system of claim 11 wherein the catheter has a pigtail-shaped tip.

15. A method for aiding implantation of a heart valve annuloplasty ring, the method comprising:
   delivering a reference ring in straight delivery configuration constrained within a delivery catheter to a location near a heart valve;
   extending the reference ring through an exit port of the delivery catheter such that the reference ring elastically recovers a pre-formed deployment configuration;
   positioning the reference ring in inferior abutment with an annulus of the heart valve without passing the reference ring through the annulus of the heart valve;
   viewing an image of the inferiorly positioned reference ring while implanting the annuloplasty ring; and
   retracting the extended reference ring into the delivery catheter after implantation of the annuloplasty ring to position the reference ring in the straight delivery configuration prior to removal from a body.

16. The method of claim 15 further comprising:
   inflating a balloon on the reference ring subsequent to positioning the reference ring in inferior abutment with the annulus of the heart valve; and
   extending the valve annulus around the balloon to form a shelf-like protrusion.

17. The method of claim 15 further comprising:
   retracting the reference ring into the delivery catheter.

* * * * *